United States Patent [19]
Chen et al.

[11] Patent Number: 5,891,075
[45] Date of Patent: Apr. 6, 1999

[54] CELLULOSE ESTER WOUND DRESSING

[75] Inventors: John C. Chen; Lance J. Deutsch; Paul M. Garrett, all of Charlotte, N.C.

[73] Assignee: Celanese Acetate LLC, Charlotte, N.C.

[21] Appl. No.: 886,749

[22] Filed: Jul. 1, 1997

Related U.S. Application Data

[63] Continuation of Ser. No. 496,701, Jun. 29, 1995, Pat. No. 5,685,832.

[51] Int. Cl.$^6$ .............................. A61F 13/00; A61L 15/00
[52] U.S. Cl. ........................... 602/48; 604/308; 604/304; 428/288
[58] Field of Search .............................. 602/48; 604/308, 604/304; 428/288

[56] References Cited

U.S. PATENT DOCUMENTS 5,167,764  12/1992  Nielsen et al. ........................ 524/398

FOREIGN PATENT DOCUMENTS

| | | |
|---|---|---|
| 87 1 01823A | 8/1988 | China . |
| A-0547474 | 6/1993 | European Pat. Off. . |
| A-602617A3 | 6/1994 | European Pat. Off. . |
| A-0614671 | 9/1994 | European Pat. Off. . |
| 88/00238 | 11/1988 | France . |
| WO88/08701 | 11/1988 | WIPO . |

OTHER PUBLICATIONS

G. Majno, "*The Healing Hand Man and Wound in the Ancient World*", Harvard University Press, paperback edition, 1991, p. 186.

Johnson & Johnson of New Brunswick, NJ has marketed "Adaptic" since Feb. 3, 1984.

Derwent Publications Ltd., JP1113054 *Abstraxt*.

Derwent Publications Ltd., of DE–A–3246417.

*Primary Examiner*—Jerome W. Donnelly
*Assistant Examiner*—Kelvin Hart
*Attorney, Agent, or Firm*—Walter M. Douglas

[57] ABSTRACT

A wound dressing that releases, via hydrolysis and in a controlled manner, acetic acid when subjected to body temperatures and moisture, and is made from a cellulose ester substrate with a partial solvent thereon.

5 Claims, 2 Drawing Sheets

CELLULOSE ESTER WOUND DRESSING

This is a continuation of Ser. No. 08/496,701, filed Jun. 29, 1995, now U.S. Pat. No. 5,685,832.

FIELD OF THE INVENTION

The invention is directed to a wound dressing that releases acetic acid in a controlled manner and that is made from a cellulose ester and a partial solvent.

BACKGROUND OF THE INVENTION

Wound dressings made of cellulose diacetate are known. See: People's Republic of China Patent Application No. 87 1 01823A published Aug. 31, 1988. Therein, it is disclosed that a cellulose diacetate gauze wound dressing obtains beneficial results over conventional cotton gauze wound dressing because the inventive dressing does not stick to the wound. Additionally, Johnson & Johnson of New Brunswick, N.J., has marketed a non-adhering cellulose acetate, petrolatum emulsion impregnated wound dressing under the tradename "Adaptic" since Feb. 3, 1984.

Additionally, the medical advantages obtained by treating wounds with acetic acid (or vinegar) is widely known in folk medicine. See: G. Majno, "The Healing Hand Man and Wound in the Ancient World", Harvard University Press, paperback edition, 1991, page 186. A combination of vinegar and ethyl alcohol is also known to be beneficial for treating wounds. See: PCT Application FR88/00238, published Nov. 17, 1988. Therein, a therapeutic solution of vinegar, distilled water, and ethyl alcohol is used to treat burns.

The use of triacetin, trimethylene glycol diacetate, and glycol monoethylene acetate on cellulose acetate tow is known. In this known usage, triacetin, trimethylene glycol diacetate, and glycol monoethylene acetate act as plasticizers that facilitate inter-filament bonding.

There is a need for a wound dressing that can release acetic acid in a controlled manner, thereby facilitating wound healing.

SUMMARY OF THE INVENTION

A wound dressing that releases, via hydrolysis and in a controlled manner, acetic acid when subjected to body temperatures and moisture, and is made from a cellulose ester substrate with a partial solvent thereon.

DESCRIPTION OF THE DRAWINGS

For the purposes of illustrating the invention, there is shown in the drawings information about the invention; it being understood, however, that this information is provided to illuminate the invention and not to limit it.

DETAILED DESCRIPTION OF THE INVENTION

"Wound dressing", as used herein, refers to a bandage or the like which covers and protects wounds, for example: abrasions, cuts or burns. The inventive wound dressing is not impregnated with a petrolatum emulsion.

"Cellulose ester", as used herein, refers to organic esters. Examples of such esters include: cellulose acetate; cellulose propionate; cellulose butyrate; cellulose acetate propionate; cellulose acetate butyrate; cellulose propionate butyrate; and the like; and combinations thereof. The cellulose esters useful in the present invention can be prepared by any known technique. See: Kirk-Othmer, *Encyclopedia of Chemical Technology*, 3rd Edition, Vol. 5, John Wiley & Sons, New York, NY, 1979, p. 89–129; and Libscomb, A. G., *Cellulose Acetate: Its Manufacture and Applications*, Ernest Benn, Ltd. London, GB, 1933, both are incorporated herein by reference. The cellulose esters of the present invention preferably have at least 2 anhydroglucose rings and most preferably have from about 2 to 5,000 anhydroglucose rings. Also, such polymers typically have an inherent viscosity (IV) of about 0.2 to about 3.0 deciliters per gram, most preferably about 1 to 1.6, as measured at a temperature of 25° C. from a 0.5 gram sample and 100 ml of a 60/40 by weight solution of phenol/tetrachloroethane. In addition, the DS/AGU (degree of substitution per anhydroglucose unit) of the cellulose esters useful herein ranges from about 1.5 to about 2.7. Cellulose acetates having a DS/AGU of 1.7 to 2.6 are especially preferred. The most preferred cellulose acetate has a DS/AGU of 1.8 to 2.2 and an IV of 1.3 to 1.5.

The foregoing cellulose esters may contain delustrants (e.g., titanium dioxide) and spin finishes as is well known.

"Substrate", as used herein, refers to fabric (woven or knitted) or film forms of cellulose esters and excludes tows or yarns unless in woven or knitted form. For example, the cellulose ester may be produced in a staple or filament form, then spun into yarns, and the yarns may be woven or knitted into fabrics. Alternatively, the cellulose ester may be formed into a film. The film maybe porous, e.g., microporous. A gauze is preferred.

"Partial solvent", as used herein, refers to, for example, glycerol triacetate (also known as, triacetin), trimethylene glycol diacetate, glycol monoethyl ether acetate, and combinations thereof. Triacetin is preferred. The solvent may be sprayed onto the cellulose ester substrate. The solvent may comprise about 4–15% by weight of the substrate. Preferably, the solvent comprises about 10% by weight of the substrate.

"Body temperature and moisture" refers to the conditions that are typically found at or around the wound, for example, the temperature at or around a wound of the human body may be about 98.6±5° F.

Figure 1:
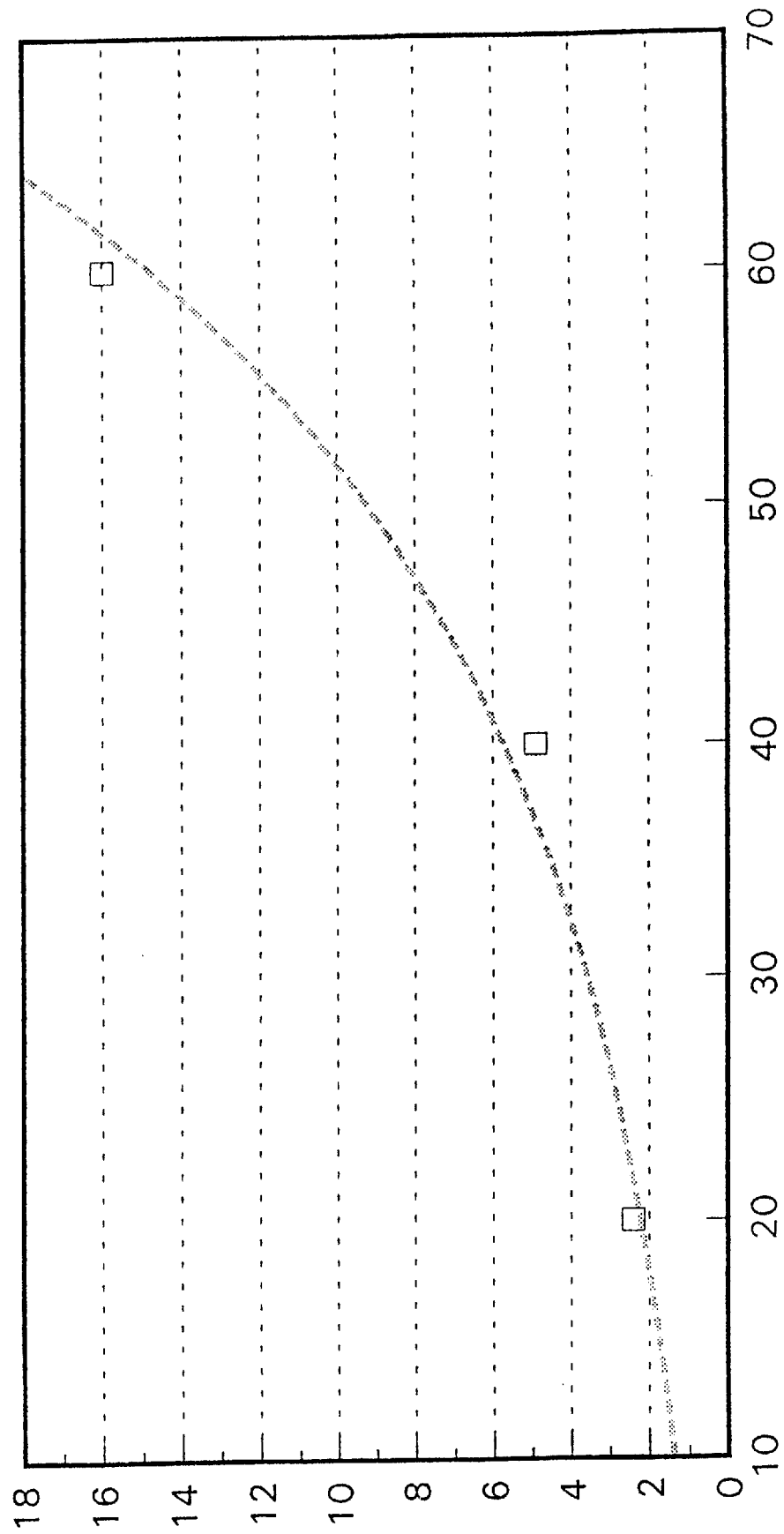
FIG. 1 is a graphical representation of the release of acetic acid (milligrams (mg) acid per gram (g) dressing per day) as a function of temperature (0° C.) from one embodiment of the present invention.
Figure 2:
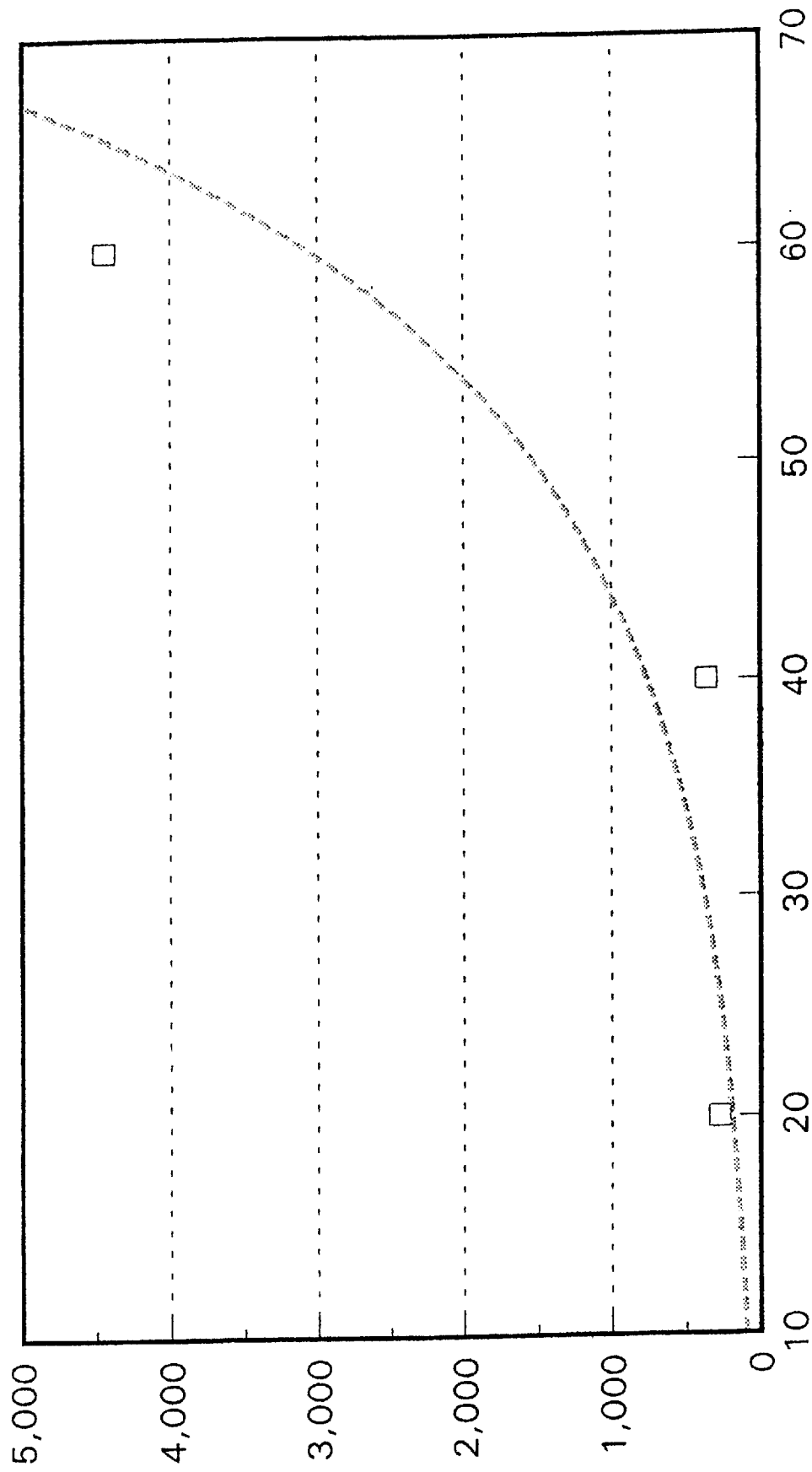
FIG. 2 is a graphical representation of the release of acetic acid (micrograms (mcg) acid per gram (g) cellulose acetate per day) as a function of temperature (0° C.) from cellulose acetate having a degree of substitution of about 2.5.

The present invention is able to release acetic acid, via hydrolysis, in a controlled manner. Specifically, the dressing releases acetic acid at a rate greater than 1000 micron grams per day. Preferably, the inventive wound dressing releases about 4 to 6 milligrams per day. FIG. 1 illustrates that cellulose ester fibers (e.g. cellulose acetate, DS/AGU=2.5) with a partial solvent (i.e., triacetin) thereon, release a great amount of acetic acid. FIG. 2 illustrates that untreated cellulose ester fibers (e.g. cellulose acetate, DS/AGU=2.5) release minor amount of acetic acid.

The present invention is further explained with reference to the non-limiting examples below.

EXAMPLES

Example 1 (COMPARATIVE)

Cellulose acetate having a degree of substitution of approximately 2.5 is heated to a constant temperature of 100° C. at a relative humidity of nearly 100%. Hydrolysis of cellulose acetate under these conditions yields approximately 400 micrograms per gram of cellulose acetate per day. Note: FIG. 2.

Example 2

At 10% by weight of triacetin (glycerol triacetate) is added to the cellulose acetate described in Example 1. The treated cellulose acetate is subjected to the same conditions as in Example 1. Approximately 4.5 milligrams cellulose acetate/triacetin is formed for a day. Note: FIG. 1.

The present invention may be embodied in other specific forms without departing from the spirit or essential attributes thereof and, accordingly, reference should be made to the appended claims, rather than to the foregoing specification, as indicating the scope of the invention.

We claim:

1. A wound dressing comprising a cellulose ester substrate and a partial solvent thereon, wherein said substrate is a knitted fabric, wherein said dressing releases, via hydrolysis of said cellulose ester at 98.6±5° F. and in a controlled manner, acetic acid.

2. The dressing of claim 1 wherein the partial solvent is selected from the group consisting of: glycerol triacetate, trimethylene glycol diacetate, glycol monoethylene acetate, and combinations thereof.

3. The wound dressing of claim 2 wherein the partial solvent is glycerol triacetate.

4. The wound dressing according to claim 1 wherein the dressing releases greater than 1000 micrograms per day of acetic acid.

5. The dressing of claim 1 wherein the cellulose ester is cellulose acetate having a degree of substitution of about 2.5 per anhydroglucose unit.

* * * * *

Disclaimer 5,891,075—John C. Chen; Lance J. Deutsch; Paul M. Garrett, all of Charlotte, N.C. (US) CELLULOSE ESTER WOUND DRESSING Patent dated Apr. 6, 1999. Disclaimer filed Mar. 22, 2004, by the assignee, Chen et al.

Hereby enters this disclaimer to claims 1-5 of said patent.

(*Official Gazette March 15, 2005*)